(12) United States Patent
Radmer et al.

(10) Patent No.: US 11,273,261 B2
(45) Date of Patent: Mar. 15, 2022

(54) INJECTION DEVICE FOR PERFORMING MEDICAL INJECTIONS

(75) Inventors: Bo Radmer, Hillerød (DK); Jakob Oest Wielandt, Copenhagen (DK); Frank Andreas Jespersen, Bagsværd (DK); Tom Hede Markussen, Bagsværd (DK); Jacob Kollerup Jensen, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 687 days.

(21) Appl. No.: 12/865,048

(22) PCT Filed: Jan. 20, 2009

(86) PCT No.: PCT/EP2009/050590
§ 371 (c)(1),
(2), (4) Date: Nov. 1, 2010

(87) PCT Pub. No.: WO2009/095332
PCT Pub. Date: Aug. 6, 2009

(65) Prior Publication Data
US 2011/0046567 A1 Feb. 24, 2011

Related U.S. Application Data

(60) Provisional application No. 61/027,093, filed on Feb. 8, 2008.

(30) Foreign Application Priority Data

Jan. 28, 2008 (EP) .................................... 08100987

(51) Int. Cl.
*A61M 5/31* (2006.01)
*A61M 5/24* (2006.01)
*A61M 5/315* (2006.01)

(52) U.S. Cl.
CPC ............ *A61M 5/3146* (2013.01); *A61M 5/24* (2013.01); *A61M 5/31511* (2013.01);
(Continued)

(58) Field of Classification Search
CPC .. A61M 2005/2407; A61M 2005/2433; A61M 5/2455; A61M 2005/2485;
(Continued)

(56) References Cited

U.S. PATENT DOCUMENTS 3,577,980 A 5/1971 Cohen
3,941,129 A 3/1976 Pleznac
(Continued)

FOREIGN PATENT DOCUMENTS

DE 19519147 A1 12/1995
EP 1074273 9/2004
(Continued)

OTHER PUBLICATIONS

Webster's New World College Dictionary Fourth Edition 2001, Michael Agnes, Editor in Chief, Embed Definition. pp. 1-3.
European Patent Application EP08100987.0, filed Jan. 28, 2008.

*Primary Examiner* — Shefali D Patel
(74) *Attorney, Agent, or Firm* — Wesley Nicolas (57) ABSTRACT

The present invention concerns a prefilled injection device having a container and a dose setting mechanism encapsulated inside a housing. The injection device incorporates an axial variable connection such that a distance between a distal end of a piston rod and a plunger is minimized preferably to zero.

2 Claims, 4 Drawing Sheets

(52) U.S. Cl.
CPC ....... *A61M 5/31515* (2013.01); *A61M 5/3129* (2013.01); *A61M 2005/2407* (2013.01); *A61M 2005/2488* (2013.01); *A61M 2207/00* (2013.01)

(58) Field of Classification Search
CPC ...... A61M 2005/2488; A61M 5/31515; A61M 5/31533; A61M 5/24; A61M 5/2422; A61M 5/3129; A61M 5/3146; A61M 5/315; A61M 5/31511; A61M 2005/2403; A61M 2005/3142; A61M 2207/00; A61M 2207/10
USPC ........ 604/207, 208, 209, 210, 211, 218, 228
See application file for complete search history.

(56) References Cited

U.S. PATENT DOCUMENTS

| | | | |
|---|---|---|---|
| 4,883,466 A * | 11/1989 | Glazier | A61M 5/5066 604/110 |
| 4,973,309 A | 11/1990 | Sultan | |
| 5,114,406 A | 5/1992 | Gabriel et al. | |
| 5,688,251 A * | 11/1997 | Chanoch | A61M 5/3146 222/309 |
| 5,695,472 A | 12/1997 | Wyrick | |
| 6,004,297 A | 12/1999 | Steenfeldt-Jensen et al. | |
| 6,241,709 B1 | 6/2001 | Bechtold et al. | |
| 6,485,465 B2 | 11/2002 | Moberg et al. | |
| 2003/0004466 A1 | 1/2003 | Bitdinger et al. | |
| 2004/0215153 A1 | 10/2004 | Graf et al. | |
| 2006/0178634 A1 | 8/2006 | Wyrick | |
| 2007/0191784 A1 | 8/2007 | Jacobs et al. | |

FOREIGN PATENT DOCUMENTS

| | | |
|---|---|---|
| EP | 1776975 A2 | 4/2007 |
| EP | 1911479 A1 | 4/2008 |
| EP | 2247327 A1 | 11/2010 |
| GB | 806703 | 12/1958 |
| JP | 2004535254 A | 11/2004 |
| JP | 2005073985 A | 3/2005 |
| JP | 2007502146 A | 2/2007 |
| RU | 2132704 C1 | 7/1999 |
| WO | WO9710864 | 3/1997 |
| WO | WO9916487 | 4/1999 |
| WO | 01072357 A2 | 10/2001 |
| WO | 03/008023 A1 | 1/2003 |
| WO | 2005018721 A1 | 3/2005 |
| WO | 2005/044346 A2 | 5/2005 |
| WO | 2005097233 | 10/2005 |
| WO | 2006074171 A1 | 7/2006 |
| WO | 2007017051 A1 | 2/2007 |
| WO | WO2008003560 | 1/2008 |

* cited by examiner

INJECTION DEVICE FOR PERFORMING MEDICAL INJECTIONS

CROSS-REFERENCE TO RELATED APPLICATIONS

This application is a 35 U.S.C. § 371 national stage application of International Patent Application PCT/EP2009/050590 (published as WO 2009/095332), filed Jan. 20, 2009, which claimed priority of European Patent Application 08100987.0, filed Jan. 28, 2008; this application further claims priority under 35 U.S.C. § 119 of U.S. Provisional Application 61/027,093, filed Feb. 8, 2008.

THE TECHNICAL FIELD OF THE INVENTION

The invention relates to a variable connection for an injection device and preferably for a variable connection between the parts of an injection device determining the distance between the movable element in the container and the part moving the movable part.

DESCRIPTION OF RELATED ART

People suffering from diabetes are often treated with multiple daily injections in a regimen comprising one or two daily injections of a long acting insulin to cover the basal requirement supplemented by bolus injections of a short or rapid acting insulin to cover requirements related to meals.

Generally speaking two different types of pen systems are used for the treatment of diabetes. The first type of system being injection devices with a replaceable cartridge containing the insulin to be injected. Often such cartridges contain 3 ml of insulin, and when this amount has been injected a new cartridge is inserted in the same injection device which therefore often is in use for several years. Such injections devices are usually referred to durable injection devices.

An example of such durable injection device where the cartridge is connected to the injection device by way of a bayonet coupling is e.g. disclosed in WO 99/16487.

The other type being injection devices containing a predetermined and non-replaceable amount of insulin, also often 3 ml. The insulin is often contained in a cartridge embedded in the injection device. When the predetermined amount has been injected which can take anywhere from a few days to a month, the entire injection device is discarded and a new injection device is used for subsequent injections. Such injection devices are often referred to as disposable or prefilled injection pens. The present invention lies within this type of injection devices.

An example of such prefilled injection pen where the two parts forming the housing is irreversible clicked together thereby encapsulating the container is known from U.S. Pat. No. 6,004,297 and from WO 2008/003560.

When clicking the parts of an injection device together the tolerances must be calculated such that the click- or snap function will always be activated i.e. the tolerances must be such that the "point of no return" is always reached during assembly otherwise the injection device will fall apart. At the same time the distal end of the piston rod means must not be pressed against the plunger while this will pressurize the content in the cartridge with the result that the liquid drug will start to flow from the injection device once an injection needle is mounted to the needle mount.

Not only does the individual parts making up the injection device come with certain tolerances, also when filing the liquid drug into the cartridge a certain tolerance obliges, both in regard of the cartridge itself and in regard of the volume of the content, which results in a slightly different position of the plunger from one cartridge to another.

Due to these production tolerances there must always be sufficient space between the plunger of the cartridge and the distal end of the piston rod means of the dose setting and injection mechanism to absorb the tolerances and to allow the "point of no return" to be reached during the assembly of the injection device in all cases.

As a result of this the assembled injection device will always be delivered to its final user with a distance between the plunger and the distal end of the piston rod means, a distance that will vary for each single injection device. The user must therefore make an initial priming of the injection device before first use i.e. the user must perform one or more air shoots before the first use of the device such that the distal end of the piston rod means are moved into abutment with the rubber plunger.

For injection devices operating with large dose sizes this is critical, since the air shoots are based on the large dose size. When the user executes the last air shoot bringing the piston rod means into abutment with the plunger this shoot can be larger than the remaining distance between the piston rod means and the plunger resulting in a forward movement of the plunger and a significant loss of fluid drug.

DESCRIPTION OF THE INVENTION

It is an object of the present invention to provide an injection device in which initial priming can be avoided.

By determining the distance between the distal end of the piston rod means and the plunger of the cartridge individually during assembly, the device can be assembled such that this distance is minimized, preferably minimized to zero such that the piston rod means abuts the plunger. The individual adjustment of this distance can be practised in many different ways, one way could be to have the piston rod means comprise two parts which can be adjusted relative to each other in the axial direction during assembly, another could be to have the housing comprise of two parts which can be adjusted relative to each other during assembly.

The piston rod means could e.g. be made from a piston rod and a piston rod foot which has an interface that can slide axially. Once the piston rod and the piston rod foot are slid into the correct position the two elements are permanently connected to each other, preferably by welding.

In one embodiment the piston rod foot is provided with a number of wings that engages a number of recesses in the piston rod, which recesses preferably has a sloping configuration such that the piston rod foot is urged in the distal direction.

In a different embodiment, the apparatus for performing medical injections comprises, a housing, a container containing the liquid medicament and a dose setting and injection mechanism for setting and injecting a dose of the liquid medicament, The container and the dose setting and injection mechanism are encapsulated inside the housing, which comprises a first part and a second part locked together by a longitudinal variable connection.

By using a variable connection that can be locked in a variable position, the distance between the dose setting and injection mechanism and the container can be differentiated in each device and thereby minimized in accordance with the tolerances for the specific injection device.

The two parts is preferably permanently secured to each other in the variable position thereby permanently embedding the dose setting and injection mechanism and the container.

The dose setting and injection mechanism comprises the piston rod and the container comprises a plunger, and the distance between these two parts are, according to the invention sought minimized.

The two parts making up the housing is permanently locked to each other when the piston rod and the plunger are in abutment thereby setting the distance between the piston rod means and the plunger top zero.

When the distance between the distal end of the piston rod means and the plunger are based on a relative axial movement between the parts making up the housing, the method comprises the steps of:
 (i) Bringing the piston rod means in abutment with the plunger,
 (ii) Securing the first part of the housing and the second part of the housing in this position.

Whereas when the axial distance is based on a relative axial movement between the parts making up the piston rod means, the method comprises the steps of:
 (i) Bringing the piston rod means in abutment with the plunger,
 (ii) Securing the piston rod means in this position.

As an alternative to providing the relative axial movement between the piston rod and the piston rod foot, the piston rod means can be telescopic and locked together during the assembly.

The system that makes up a prefilled injection device usually comprises two parts, a dose setting and injection mechanism which are contained in a first body part of the housing and a cartridge which is embedded in a second body part of the housing, often referred to as the cartridge holder.

According to the present invention this system further comprises means for varying the distance between the piston rod means of the dose setting and injection part and the plunger of the cartridge holder part.

These means can be provided in the piston rod means such as between the piston rod and the piston rod foot or alternatively be provided between the first body part and the second body part of the housing.

These detailed described embodiments do not exclude other ways of incorporating the means for varying the distance in an injection device.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and Cpeptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid. An "injection needle" usually comprises a "needle cannula" and a "hub". The term "Needle Cannula" is used to describe the actual conduit performing the penetration of the skin during injection. A needle cannula is usually made from a metallic material such as stainless steel and connected to a hub to form an injection needle assembly. A needle cannula could however also be made from a polymeric material or a glass material. The "hub" being the part in which the needle cannula is mounted carries the connecting means for connecting the needle cannula to an injection apparatus. A hub is usually moulded from a suitable thermoplastic material. An "injection needle" is also sometime referred as a "needle assembly" i.e. comprising a needle cannula mounted in a hub as supplied to the user.

"Cartridge" is the term used to describe the container containing the liquid drug e.g. insulin. Cartridges are usually made from glass but could also be moulded from any suitable polymer. A cartridge or ampoule is preferably sealed at one end by a pierceable membrane which can be pierced e.g. by an injection needle. The opposite end is closed by a plunger made from rubber or a suitable polymer. The plunger can be slidable moved inside the cartridge. The space between the pierceable membrane and the movable plunger holds the liquid drug which is pressed out as the plunger decreased the volume of the space holding the liquid drug.

"Piston rod means" is the term used to describe the mechanical element that transfer force from the dosing mechanism to the plunger inside the cartridge thereby moving the plunger forward. The "piston rod means" usually comprises a piston rod and a piston rod foot which is typically the element abutting the plunger. The piston rod and the piston rod foot can be made as two separate pieces or they can be made as one integral element. The "piston rod means" could also only be the piston rod without any foot in which case the piston rod would abut directly on the plunger.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
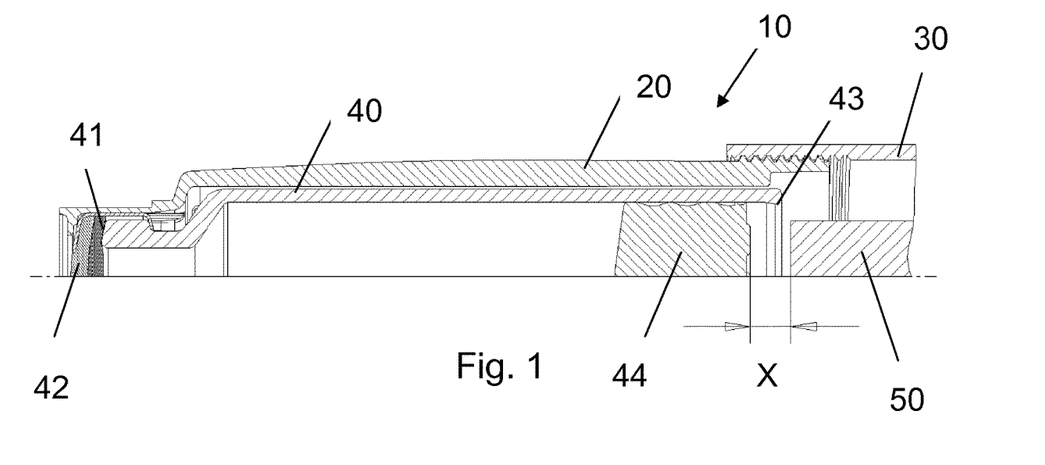
FIG. 1 shows a cross section of the injection device.

FIG. 1 discloses a pen shaped injection device 1 comprising a housing 10 formed from two parts 20, 30. A first part 20 holding the cartridge 40 and a second part 30 comprising a dose setting and injection mechanism which comprises a piston rod means 50.

The cartridge 40 which contains the liquid medicament to be expelled is at a first end 41 provided with a membrane 42 which is pierceable by a not shown injection needle and a second end 43 which is locked by a movable plunger 44. When a user activates the dose setting and injection mechanism to set and inject a dose, the piston rod means 50 is moved forward into contact with the plunger 44 which it then continues to move forward thereby expelling the set dose through the injection needle.

Figure 2:
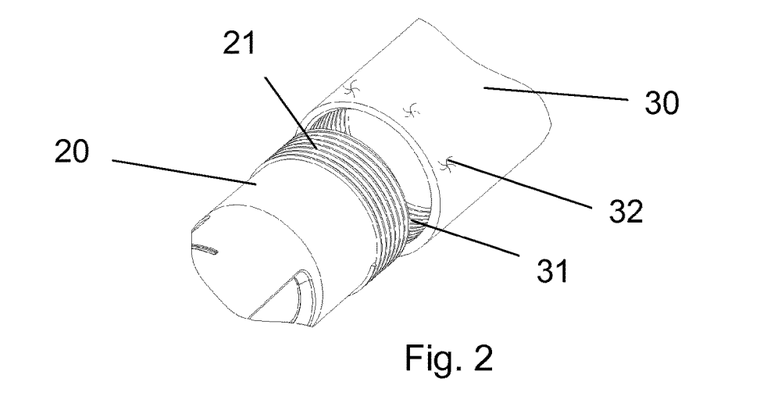
FIG. 2 shows a perspective view of an assembly of the housing.

The first part 20 is at its proximal end provided with a number of outwardly pointing ratchet teeth 21 which as disclosed in FIG. 2 can surround the entire periphery of the first part 20.

The second part 30 is at its distal end provided with corresponding inwardly pointing ratchet teeth 31. Instead of providing the inwardly pointing ratchet teeth 31 and the outwardly pointing ratchet teeth 21 around the entire periphery, the teeth 21, 31, could be provided only on a part of the periphery.

When the proximal end of the first part 20 enter the distal end of the second part 30 in order to assemble the housing 10, the outwardly pointing ratchet teeth 21 engages the inwardly pointing ratchet teeth 31 on the second part 30 thereby preventing the two part 20, 30 from being separated. The two parts 20, 30 can be variable adjusted relatively to each other such that the distance X between the piston rod means 50 and the plunger 44 can be minimized.

Once the first part 20 and the second part 30 is in a position where a satisfactory distance X is obtained the two parts 20, 30 can be irreversible locked to each other. This irreversible locking can be performed in a number of different ways.

In FIG. 2 the two parts 20, 30 are permanently secured to each other by deforming zones 32 of the second part 30. This deformation can be done by pressure or by heat deformation.

Figure 3:
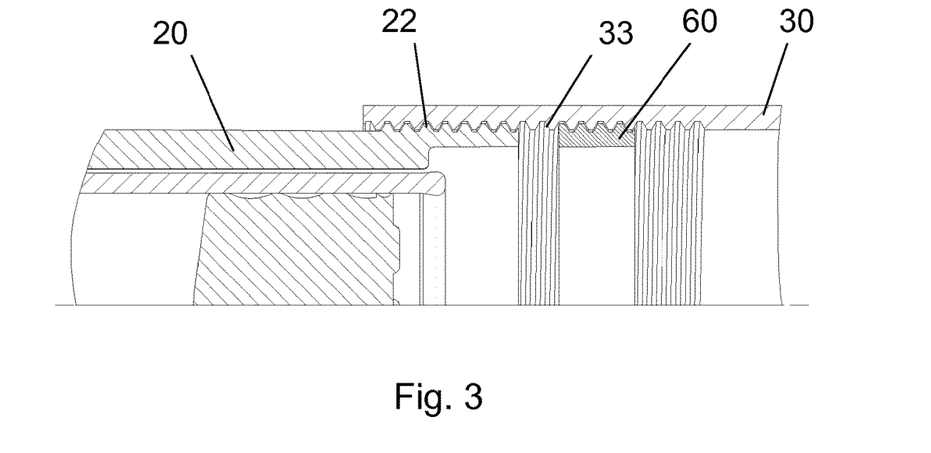
FIG. 3 shows a cross sectional view of an alternatively assembly of the housing.

A solution based on a counter nut 60 is disclosed in FIG. 3. The first part 20 and the second part 30 is provided with engaging threads 22, 33 such that the two parts 20, 30 are moved closer to each other when rotated. When the final position is reached, the counter nut 60 is screwed in the distal direction until it abuts the first part 20 thereby locking the two parts 20, together.

Figure 4:
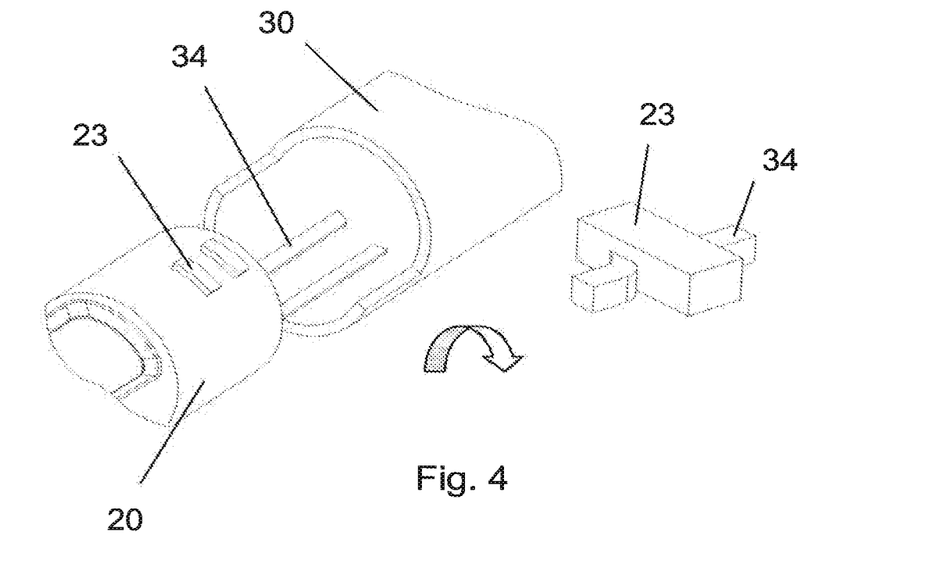
FIG. 4 shows a perspective view of an alternatively assembly of the housing.

In the embodiment disclosed in FIG. 4, the first part 20 is provided with a number of outwardly pointing protrusions 23 and the second part 30 is provided with a number of axially located ribs 34. When the two parts are rotated relatively to each other the protrusions 23 penetrates through the ribs 34 as disclosed in the close-up figure, thereby locking the two parts 20, 30 to each other.

Figure 5:
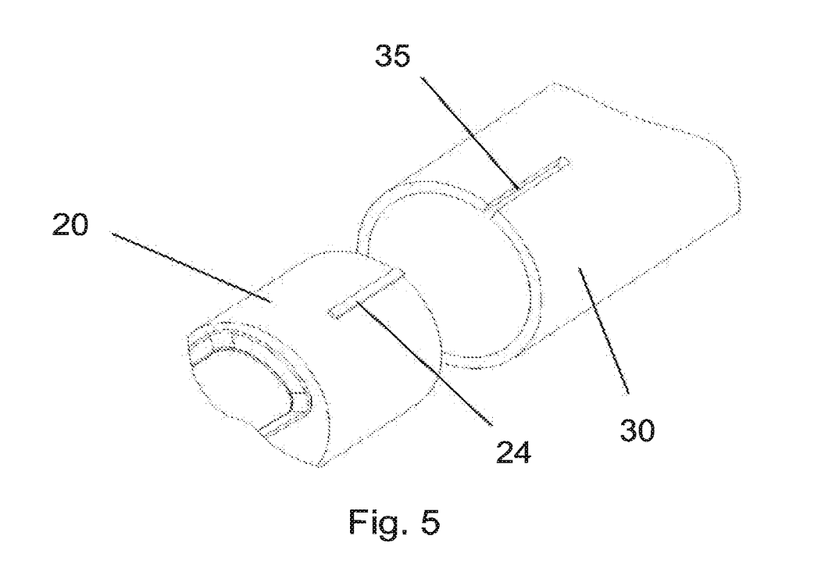
FIG. 5 shows a perspective view of an alternatively assembly of the housing.
Figure 6:
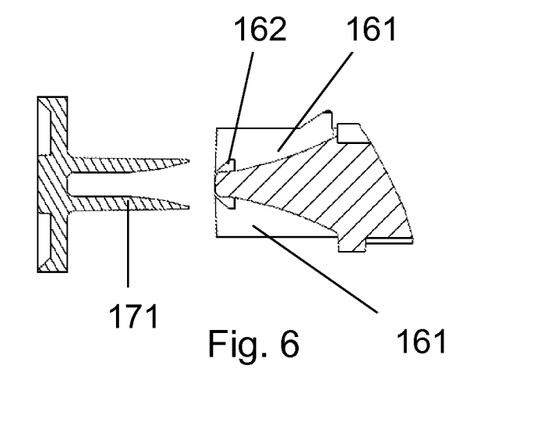
FIG. 6 shows a cross sectional view of the piston rod means prior to assembly.
Figure 7:
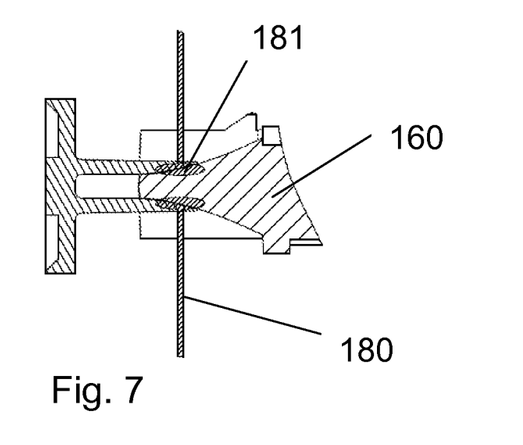
FIG. 7 shows a cross sectional view of the piston rod means in one assembled position.
Figure 8:
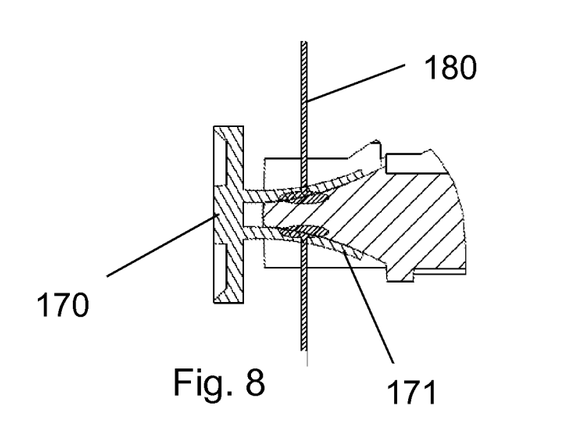
FIG. 8 shows a cross sectional view of the piston rod means in a different assembled position.
Figure 9:
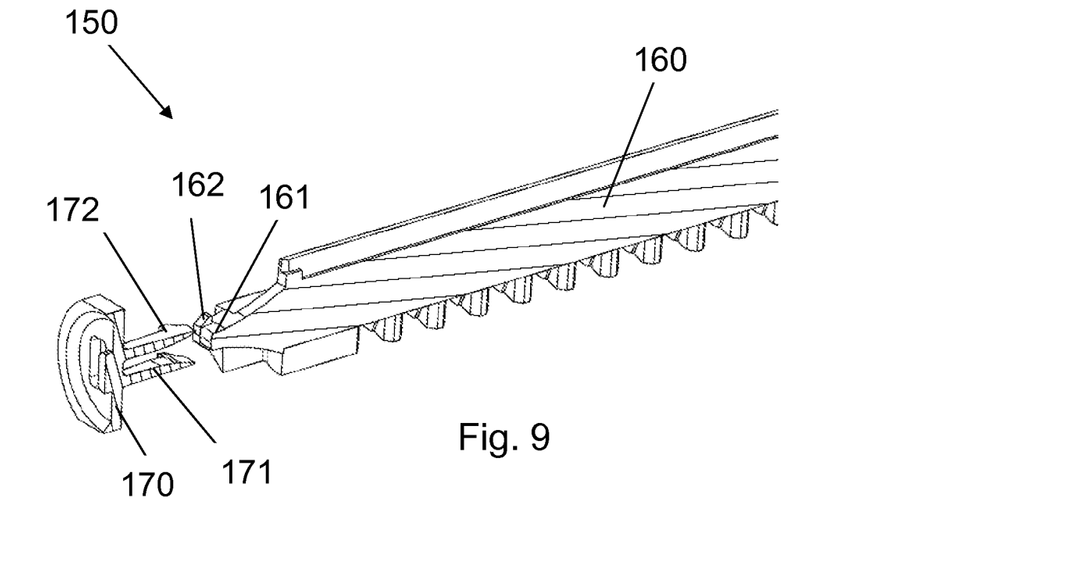
FIG. 9 shows a view of the piston rod means.

In the embodiment disclosed in FIG. 5, the first part 20 is provided with an axially extending rib 24 which during assembly engages a longitudinal slit 35 in the second part. Once the first part 20 and the second part 30 is in their final position minimizing the distance between the piston rod 50 and the rubber plunger 44 preferably to zero the two parts are attached to each other by welding the axially extending rib 24 to the second part 30 by applying heat such that the axially extending rib 24 melts in the slit 35. Alternatively glue could be applied thereby gluing the parts 20, 30 together.

The FIGS. 6 to 10 disclose an alternative way of minimizing the distance between the piston rod means 150 and the plunger 144. In the disclosed embodiment the piston rod means 150 comprises a piston rod 160 and a piston rod foot 170. The piston rod foot 170 is provided with a number of resilient attaching wings 171 pointing in the proximal direction and the piston rod 160 is provided with a number of recesses 161 for receiving the attaching wings 171. These recesses 161 have a sloping configuration sloping towards the distal end of the piston rod 160 such that the piston rod foot 170 will slide in the proximal direction when the piston rod foot 170 is mounted on the piston rod 160. Further the piston rod 160 is provided with a number of protrusions 162 engaging a number of barbs 172 on the piston rod foot 170 when it is in its most distal position thereby preventing the piston rod foot 170 from being automatically separated from the piston rod 160.

Figure 10:
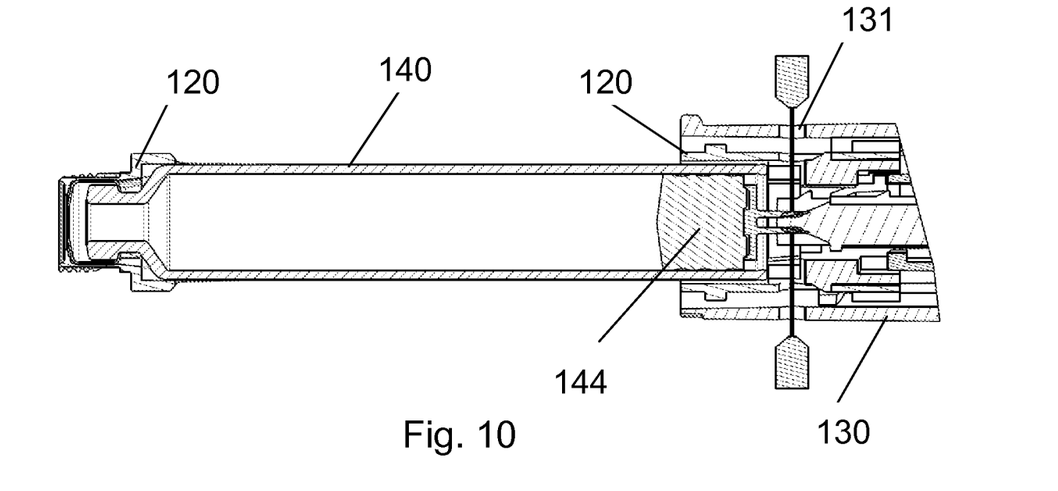
FIG. 10 show a cross section of the injection device during assembly.

The cartridge holder 20, 120 could in all the embodiments be provided with an opening or window as indicated in FIGS. 4, 5 and 10 through which the liquid drug in the cartridge 40, 140 can be viewed.

When an injection device is assembled the piston foot 170 is axially pushed onto the piston rod 160 as disclosed in FIGS. 6 to 9. Once the correct relative position between the piston rod foot 170 and the piston rod 160 is obtained a laser beam 180 is directed towards the attaching wings 171 such that a melting zone 181 between the attaching wings 171 of the piston rod foot 170 and the recesses 161 of the piston rod 161 is obtained thereby melting the piston rod foot 170 and the piston rod 160 together. Although laser welding is described in this application a number of alternative methods for attaching the two parts 160, 170 can be used. The piston rod foot 170 and the piston rod 160 could e.g. be attached to each other through a variable mechanical connection such as a threaded connection or a telescopic mechanism; alternatively the two parts 160, 170 could be glued together in their final position.

During assembly the usual procedure as disclosed in FIG. 10 would be first to assemble the dose setting and injection mechanism, thereafter attaching the piston rod foot 170 on the piston rod 160 and finally to press the cartridge holder 120 with the cartridge 140 into the position in which the cartridge holder 120 locks to the main body 130. The plunger 144 of the cartridge 140 will then move the piston rod foot 170 in the proximal direction relatively to the piston rod 160. Once the injection device is fully assembled, the piston rod foot 170 will abut the plunger 144 due the sloping interface between the piston rod foot 170 and the piston rod 160. In this abutting position the laser welding is performed through openings 131 in the main body 130 thereby locking the piston rod foot 170 to the piston rod 160 in a position where the piston rod foot 170 abuts the plunger 144 such that initial priming can be avoided.

Some preferred embodiments have been shown in the foregoing, but it should be stressed that the invention is not limited to these, but may be embodied in other ways within the subject matter defined in the following claims. The figures e.g. discloses the injection device of the present invention in the form of an oblong pen-shaped object, however, this particular shape is in no way limiting for the present invention as defined in the claims.

The invention claimed is:

1. A disposable prefilled injection device for performing medical injections comprising,
   a cartridge having a predetermined and non-replaceable amount of a medicine, the cartridge permanently embedded in the prefilled injection device containing a piston rod structure, such that when the predetermined and non-replaceable amount of the medicine has been injected the entire prefilled injection device is discarded and a new injection device is used for subsequent injections,
   wherein the cartridge comprises a distal end closed by a membrane and a proximal end closed by a movable plunger which is movable in a distal direction by the piston rod structure in order to expel the medicine contained between the membrane and the movable plunger, wherein a relative axial position between the piston rod structure and the plunger is determined during assembly of the prefilled injection device,
   the piston rod structure comprises a piston rod and a piston rod foot,
   wherein the piston rod foot is a separate part permanently attachable to the piston rod,
   wherein the piston rod foot has a variable connection allowing the piston rod foot and the piston rod to slide axially relative to one another, and
   wherein a relative axial distance between the piston rod foot and the plunger is individually determined during the assembly such that when the piston rod and the piston rod foot are slid into a position where the piston rod foot and the movable plunger abut each other, the piston rod and the piston rod foot are configured to be permanently connected to each other, and
   wherein the piston rod foot has a number of resilient attaching wings pointing in a proximal direction which wings are received in a number of recesses in the piston rod.

2. A method of assembling a prefilled injection device for performing medical injections, the prefilled injection device comprising,
   a cartridge having a predetermined and non-replaceable amount of a medicine, the cartridge permanently embedded in the prefilled injection device containing a piston rod structure, such that when the predetermined and non-replaceable amount of the medicine has been injected the entire prefilled injection device is discarded and a new injection device is used for subsequent injections,
   wherein the cartridge comprises a distal end closed by a membrane and a proximal end closed by a movable plunger which is movable in a distal direction by the piston rod structure in order to expel the medicine contained between the membrane and the movable plunger, wherein a relative axial position between the piston rod structure and the plunger is determined during assembly of the prefilled injection device,
   the piston rod structure comprises a piston rod and a piston rod foot, wherein the piston rod foot is a separate part permanently attached to the piston rod, wherein the piston rod foot has a variable connection that can slide axially allowing the piston rod foot and the piston rod to slide axially relative to one another, and
   wherein an axial distance between the piston rod foot and the plunger is individually determined during the assembly such that the piston rod foot and the movable plunger abut each other, and
   the method comprising:
   (i) bringing the piston rod structure comprising the piston rod and the piston rod foot in abutment with the plunger;
   (ii) securing the piston rod structure comprising the piston rod and the piston rod foot when the piston rod foot is in abutment with the plunger, and
   wherein an axial distance between the piston rod and the piston rod foot is variable during the assembly, and the piston rod foot is permanently secured to the piston rod during the assembly.

* * * * *

UNITED STATES PATENT AND TRADEMARK OFFICE
CERTIFICATE OF CORRECTION

| | |
|---|---|
| PATENT NO. | : 11,273,261 B2 |
| APPLICATION NO. | : 12/865048 |
| DATED | : March 15, 2022 |
| INVENTOR(S) | : Radmer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 734 days.

Signed and Sealed this
Thirteenth Day of December, 2022

Katherine Kelly Vidal
*Director of the United States Patent and Trademark Office*